(12) United States Patent
Schneider et al.

(10) Patent No.: US 7,767,598 B2
(45) Date of Patent: Aug. 3, 2010

(54) DIAPER PROVIDING PRESSURE INSENSITIVE LIQUID HANDLING

(75) Inventors: Manuela Schneider, Frankfurt (DE); Christofer Fuchs, Kronberg (DE); Olaf Van Gansewinkel, Steinbach/Ts (DE)

(73) Assignee: The Procter & Gamble Company, Cincinnati, OH (US)

( * ) Notice: Subject to any disclaimer, the term of this patent is extended or adjusted under 35 U.S.C. 154(b) by 514 days.

(21) Appl. No.: 10/913,003

(22) Filed: Aug. 6, 2004

(65) Prior Publication Data
US 2005/0043694 A1     Feb. 24, 2005

(30) Foreign Application Priority Data
Aug. 7, 2003   (EP) ................... 03018027
Oct. 15, 2003  (EP) ................... 03023345

(51) Int. Cl.
B32B 3/00    (2006.01)

(52) U.S. Cl. ............... 442/104; 442/149; 442/334; 442/352; 442/361; 442/59

(58) Field of Classification Search ........... 442/149, 442/334, 361, 59, 352, 104
See application file for complete search history.

(56) References Cited

U.S. PATENT DOCUMENTS

| | | |
|---|---|---|
| 3,860,003 A | 1/1975 | Buell |
| 4,777,433 A | 10/1988 | Steele et al. |
| 4,834,735 A | 5/1989 | Alemany |
| 4,898,642 A | 2/1990 | Moore et al. |
| 4,906,687 A | 3/1990 | Modic |
| 5,037,416 A | 8/1991 | Allen |
| 5,151,092 A | 9/1992 | Buell |
| 5,269,775 A | 12/1993 | Freeland |
| 5,509,915 A | 4/1996 | Hanson et al. |
| 5,527,302 A | 6/1996 | Endres et al. |
| 5,569,234 A | 10/1996 | Buell |
| 5,625,222 A | 4/1997 | Yoneda |
| 5,774,929 A | 7/1998 | Jurgens et al. |
| 5,997,980 A | 12/1999 | Matoba |
| 6,004,306 A | 12/1999 | Robles |

(Continued)

FOREIGN PATENT DOCUMENTS

EP     0 149 880 A2     7/1985

(Continued)

OTHER PUBLICATIONS

U.S. Appl. No. 10/912,991, filed Aug. 6, 2004, All Office Actions and Responses beginning Aug. 6, 2004.

(Continued)

*Primary Examiner*—Andrew T Piziali
*Assistant Examiner*—Peter Y Choi
(74) *Attorney, Agent, or Firm*—John G. Powell; Jay A. Krebs (57) ABSTRACT

A liquid acquisition layer having a multitude of fibers and a binder is useful in a variety of absorbent articles, such as diapers and sanitary napkins. The liquid acquisition layer has a caliper which decreases in response to external pressure and increases upon removal of said external pressure. The increase in caliper is measured by a recovery value, wherein the liquid acquisition layer recovery value at 45° C. is at least 65% of the recovery value at 20° C.

6 Claims, 2 Drawing Sheets

U.S. PATENT DOCUMENTS

| | | |
|---|---|---|
| 6,177,482 B1 | 1/2001 | Cinelli et al. |
| 6,420,626 B1 | 7/2002 | Erspamer et al. |
| 6,479,415 B1 | 11/2002 | Erspamer et al. |
| 6,479,416 B1 | 11/2002 | Erspamer et al. |
| 6,610,898 B1 | 8/2003 | Magnusson et al. |
| 6,734,335 B1 * | 5/2004 | Graef et al. ............ 604/365 |
| 2002/0016120 A1 * | 2/2002 | Nagano et al. ............ 442/352 |
| 2002/0165509 A1 | 11/2002 | Baer et al. |
| 2002/0177378 A1 | 11/2002 | Bodaghi |
| 2003/0105190 A1 | 6/2003 | Diehl |
| 2003/0130635 A1 | 7/2003 | Tate et al. |
| 2003/0225382 A1 | 12/2003 | Tombult-Meyer et al. |
| 2004/0115251 A1 | 6/2004 | Goldman et al. |
| 2004/0162536 A1 | 8/2004 | Becker et al. |
| 2005/0033252 A1 | 2/2005 | Schneider et al. |
| 2005/0033253 A1 | 2/2005 | Fuchs et al. |
| 2007/0038195 A1 | 2/2007 | Fuchs et al. |

FOREIGN PATENT DOCUMENTS

| | | |
|---|---|---|
| EP | 0 304 319 B1 | 2/1994 |
| EP | 1067228 | 1/2001 |
| EP | 1067228 A1 * | 1/2001 |
| EP | 0 752 892 B1 | 7/2001 |
| EP | 1 032 345 B1 | 4/2003 |
| EP | 1 366 825 A2 | 12/2003 |
| EP | 1 447 066 A1 | 8/2004 |
| WO | WO 98/22279 A1 | 5/1998 |
| WO | WO 98/28022 A1 | 7/1998 |
| WO | WO 99/00098 A1 | 1/1999 |
| WO | WO 00/51651 A1 | 9/2000 |
| WO | WO 02/078756 A1 | 10/2000 |
| WO | WO 03/048440 A1 | 6/2003 |

OTHER PUBLICATIONS

U.S. Appl. No. 11/582,187, filed Oct. 17, 2006, All Office Actions and Responses beginning Oct. 17, 2006.

* cited by examiner

Fig. 1

DIAPER PROVIDING PRESSURE INSENSITIVE LIQUID HANDLING

FIELD OF THE INVENTION

The present invention relates to absorbent articles such as disposable diapers, sanitary napkins and panty liners. More specifically, the present invention relates to acquisition layers and materials for such acquisition layers, which are very suitable to be used with thin products comprising a relatively high concentration of super-absorbent polymer material.

BACKGROUND OF THE INVENTION

Disposable absorbent articles are broadly available and consumers are used to a high performance for the collecting and retaining of menses (in the case of sanitary napkins or panty liners) or for the collecting and retaining urine and fecal material (in the case of e.g. disposable diapers). However, consumers do not only expect a superior absorbency behavior, but place more and more emphasis on the wearing comfort of such articles, and namely on the dryness of those articles.

Typically, such articles comprise multiple absorbent members, at least one member being primarily designed to store liquid, and at least one other member primarily designed to acquire and/or distribute liquid.

At least the storage member will often comprise super-absorbent material, which is admixed with the traditionally used pulp fiber material. Such super-absorbent materials can absorb many times (e.g. 10, 20 or 30 times) their own weight and are therefore very helpful when designing an article of improved fluid handling properties. Many recent products employ higher and higher concentrations of super-absorbent materials, that is concentrations in excess of 50% of the total weight of the storage member. These products achieve a high absorbing capacity with a very thin storage member and are thereby typically overall thin products. While super-absorbent materials can store very large amounts of liquid, they are often not able to distribute the liquid from the point of impact to more remote areas of the absorbent article and to acquire the liquid as fast as it may be received by the article.

For this reason acquisition members are used, which provide for the interim acquisition of large amounts of liquid and which often also allow for the distribution of liquid. Thereby the acquisition member plays a key role in using the whole absorbent capacity provided by the storage member.

An exemplary state of the art absorbent article, namely a sanitary napkin, is disclosed in WO 00/51651. The so-called "secondary topsheet" primarily provides for the liquid acquisition and distribution. The storage member is provided in the form of a core that can contain a high portion of super-absorbent polymer material.

State of the art absorbent articles in the form of disposable diapers are disclosed in the following co-pending applications: EP application no. 02017516.2 and EP application no. 03002677.7. The storage member of these articles may contain more than 50 weight-percent of super-absorbent polymer material, even more than 80% and in some embodiments even about 100% of the super-absorbent polymer material. While these articles are designed to have excellent fluid handling and fluid storage behavior, they may sometimes not be as comfortable to wear as some consumers would like it, namely those consumers interested in a premium product.

For achieving excellent fluid handling and fluid storage properties the respective storage members use super-absorbent materials, which are selected mostly with an emphasis on fluid handling properties. For example EP 304319 B1 (Goldman et al.) discloses the benefits of a relatively narrow distribution of the particle size of the super-absorbent polymers. The respective articles will preferably not comprise many fines, but relatively coarse particles. EP 752892 B1 (Goldman et al.) discloses an absorbent structure, which uses concentrations of super-absorbent particles in access of 60% and teaches to use super-absorbent particles of a relatively high porosity.

Materials suitable to meet the above outlined requirements for a liquid acquisition layer must meet these requirements not only in standard or ideal conditions, but in a variety of conditions, namely at different temperatures and pressures.

Those different temperatures and pressures are encountered, for example, under the in-use conditions. In use, the temperature at which the acquisition layer must operate depends both on the body temperature of the wearer and on the ambient temperature (which is typically below the body temperature, but in some climates can also exceed the body temperature). Most pressure on the liquid acquisition layer is typically exerted when a wearer is sitting. The temperature depends on the body weight of the wearer but can also largely depend on the surface on which the wearer sits.

Other relevant conditions regarding the performance of liquid acquisition layer are those conditions of storage and transport. In one aspect, this includes the conditions under which the diapers once produced are stored and transported. Typically a diaper package exerts some compressive force onto the diaper and, depending largely on the country of marketing, may undergo a rather large range of temperatures, before being delivered to the consumer. It is important, that the liquid acquisition layer irrespective of its storage and transport history recovers to a condition, which allows for optimal liquid handling. In a second aspect, the transport and storage conditions of the material to be formed into a liquid acquisition layer before the manufacturing of the diaper are also relevant. Very often, these materials are provided as roll stock materials. To allow for economic handling and transport the material is wound onto a roll under some pressure. The respective rolls my also be stored over a relatively long period of time, and while being stored or transported be exposed to a large variety of ambient temperatures. Of course, irrespective also of the storage and transport history a material may have undergone in these earlier stages of its lifetime, a material must recover, such that optimal liquid handling performance is achieved when the material is ultimately used as a liquid acquisition layer and expected to perform in a diaper.

U.S. Pat. No. 5,997,980 (Matoba et al.) discloses the use of hollow polyester fibers for providing a nonwoven material, the hollow polyester fibers having a relatively large hollow volume of 40% to 85%. The material is said to have a high resistance to compression and a high recovery from compression.

EP 1 032 345 B1 discloses a fluid acquisition-transfer layer for an absorbent article which comprises a mixture of heat-shrunk, spiralized, thermoplastic multi-component, preferably, bi-component, functional fibers. WO 03/048440 (Brown et al.) discloses the use of similar fibers for a nonwoven fabric for a use in personal care absorbent articles, the fibers namely being single polymer, helically crimped fibers.

WO 98/22279 (Flohr et al.) discloses acquisition layers for improved liquid handling in absorbent articles. As a preferred fluid handling material fibrous materials, which are preferably carded are disclosed. These fibers are chemically bonded by a resin. The disclosed resins are more hydrophilic than the base polymer and are non-uniformly distributed in the fluid handling material throughout the thickness (z-direction). The fluid handling material is designed to achieve an acquisition performance of less than 2 seconds for the third impacting gush of liquid. The disclosed acquisition layer materials are disclosed as being easy to handle and easy to transport without requiring a large volume.

EP 149 880 (Kwok) discloses non-woven webs of synthetic fibers consolidated by means of carboxylated styrene-butadiene lattices, and disposable articles make therefrom. The obtained non-wovens are described as having improved wet tensile and elongation properties.

US 2003/0105190 (Diehl et al.) discloses a latex for utilization as a binder for nonwoven applications and a process for preparing such latex. The latex is essentially of the styrenebutadiene type.

It is one objective of the present invention to provide an absorbent article, which has improved liquid handling characteristics as compared to the above disclosed articles.

Moreover, it is an objective of the present invention to provide fluid acquisition layers for improved liquid handling characteristics, namely for use with storage layer comprising a high concentration of super absorbent polymers.

In one further important aspect it is an objective of the present invention to provide an article, which is more comfortable to wear, and which in particular provides superior dryness.

SUMMARY OF THE INVENTION

The present invention relates to absorbent articles, such as diapers and sanitary napkins, and acquisition layers useful for such articles. More specifically, the invention relates to an acquisition layer for an absorbent article, the liquid acquisition layer comprising a multitude of fibers and a binder, the liquid acquisition layer having a caliper which decreases in response to external pressure and increases upon removal of said external pressure. In accordance with the present invention the increase in caliper is measured by the recovery value as defined herein and the liquid acquisition layer recovery value at 45° C. is at least 65% of the recovery value at 20° C.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

DETAILED DESCRIPTION OF THE INVENTION

Definitions

As used herein, the following terms have the following meanings:

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinent briefs, training pants, diaper holders and liners, sanitary napkins and the like. Absorbent articles also include wipes, such as household cleaning wipes, baby wipes, and the like.

"Disposable" is used herein to describe articles that are generally not intended to be laundered or otherwise restored or reused i.e., they are intended to be discarded after a single use and, preferably, to be recycled, composted or otherwise disposed of in an environmentally compatible manner.

"Disposed" is used to mean that an element(s) is formed (joined and positioned) in a particular place or position as a unitary structure with other elements or as a separate element joined to another element.

"Diaper" refers to an absorbent article generally worn by infants and incontinent persons about the lower torso.

The terms "thickness" and "caliper" are used herein interchangeably.

"Attached" or "Joined" encompasses configurations whereby an element is directly secured to another element by affixing the element directly to the other element, and configurations whereby an element is indirectly secured to another element by affixing the element to intermediate member(s) which in turn are affixed to the other element.

"Comprise," "comprising," and "comprises" is an open ended term that specifies the presence of what follows e.g. a component but does not preclude the presents of other features, elements, steps or components known in the art, or disclosed herein.

The term "hydrophilic" describes fibers or surfaces of fibers, which are wettable by aqueous fluids (e.g. aqueous body fluids) deposited on these fibers. Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A fiber or surface of a fiber is said to be wetted by a fluid (i.e. hydrophilic) when either the contact angle between the fluid and the fiber, or its surface, is less than 90°, or when the fluid tends to spread spontaneously across the surface of the fiber, both conditions are normally coexisting. Conversely, a fiber or surface of the fiber is considered to be hydrophobic if the contact angle is greater than 90° and the fluid does not spread spontaneously across the surface of the fiber.

The terms "fiber" and "filament" are used interchangeably.

The terms "nonwoven", "nonwoven fabric" and "nonwoven web" are used interchangeable.

Absorbent Articles

Figure 1:
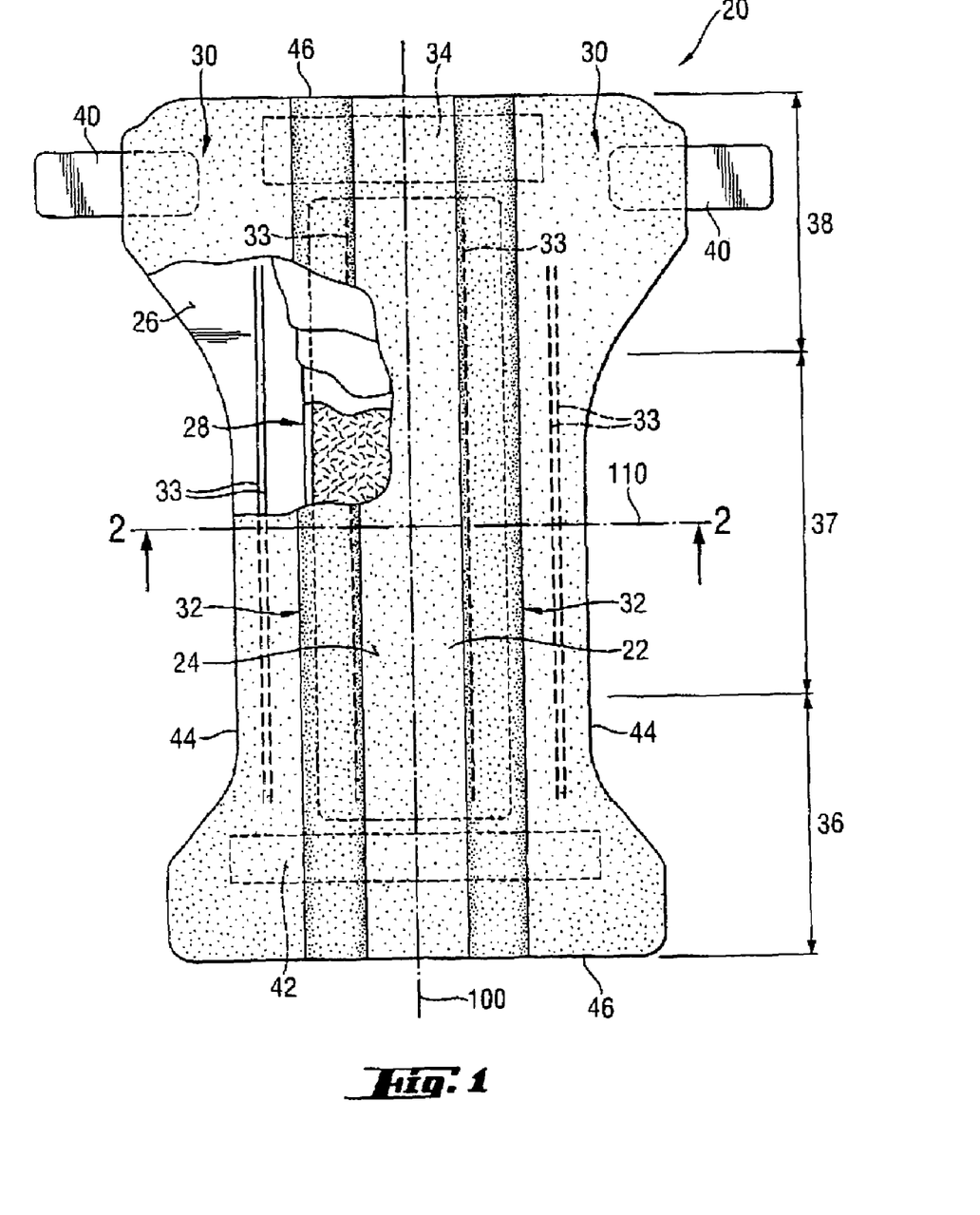
FIG. 1 is a top plan view of a disposable diaper, with the upper layers partially cut away.

FIG. 1 is a plan view of a diaper 20 as a preferred embodiment of an absorbent article according to the present invention. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20. The chassis 22 comprises an outer covering including a liquid pervious topsheet 24 and/or a liquid impervious backsheet 26. The chassis may also include most or all of the absorbent core 28 encased between the topsheet 24 and the backsheet 26. The chassis preferably further includes side panels 30, leg cuffs 32 and a waist feature 34. The leg cuffs and the waist feature typically comprise elastic members 33. One end portion of the diaper 20 is configured as the front waist region 36 of the diaper 20. The opposite end portion is configured as the rear waist region 38 of the diaper 20. An intermediate portion of the diaper 20 is configured as the crotch region 37, which extends longitudinally between the front and rear waist regions 36 and 38. The crotch region 37 is that portion of the diaper 20 which, when the diaper 20 is worn, is generally positioned between the wearer's legs. The waist regions 36 and 38 may include a fastening system comprising fastening members 40 preferably attached to the rear waist region 38 and a landing zone 42 attached to the front waist region 36. The diaper 20 has a longitudinal axis 100 and a transverse axis 110. The periphery of the diaper 20 is defined by the outer edges of the diaper 20 in which the longitudinal edges 44 run generally parallel to the longitudinal axis 100 of the diaper 20 and the end edges 46 run generally parallel to the transverse axis 110 of the diaper 20.

For unitary absorbent articles, the chassis 22 comprises the main structure of the diaper with other features added to form the composite diaper structure. While the topsheet 24, the backsheet 26, and the absorbent core 28 may be assembled in a variety of well-known configurations, preferred diaper configurations are described generally in U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 24 in FIG. 1 may be fully or partially elasticized or may be foreshortened to provide a void space between the topsheet 24 and the absorbent core 28. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 26 in FIG. 1 is generally the portion of the diaper 20 positioned with the absorbent core 28 between the backsheet 26 and the topsheet 24. The backsheet 26 may be joined with the topsheet 24. The backsheet 26 prevents the exudates absorbed by the absorbent core 28 and contained within the article 20 from soiling other external articles that may contact the diaper 20, such as bed sheets and undergarments. In preferred embodiments, the backsheet 26 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE.

The absorbent core 28 in FIG. 1 generally is disposed between the topsheet 24 and the backsheet 26. The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers, absorbent gelling materials, or any other known absorbent material or combinations of materials. The absorbent core may further comprise minor amounts (typically less than 10%) of non-liquid absorbent materials, such as adhesives, waxes, oils and the like.

Exemplary absorbent structures for use as the absorbent assemblies are described in U.S. Pat. No. 4,834,735, entitled "High Density Absorbent Members Having Lower Density and Lower Basis Weight Acquisition Zones", issued to Alemany et al. on May 30, 1989; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997.

The diaper 20 may also include such other features as are known in the art including front and rear ear panels, waist cap features, elastics and the like to provide better fit, containment and aesthetic characteristics. Such additional features are well known in the art and are described in U.S. Pat. No. 3,860,003 entitled "Contractable side portions for disposable diaper" issued to Buell et al. on Jan. 14, 1975 and U.S. Pat. No. 5,151,092 entitled "Absorbent article with dynamic elastic waist feature having a predisposed resilient flexural hinge" issued to Buell et al. on Sep. 29, 1992.

In order to keep the diaper 20 in place about the wearer, the waist regions 36 and 38 may include a fastening system comprising fastening members 40 preferably attached to the rear waist region 38. In a preferred embodiment the fastening system further comprises a landing zone 42 attached to the front waist region 36. The fastening member is attached to the front waist region 36, preferably to the landing zone 42 to form leg openings and an article waist.

Diapers 20 according to the present invention may be provided with a re-closable fastening system or may alternatively be provided in the form of pant-type diapers.

The fastening system and any component thereof may include any material suitable for such a use, including but not limited to plastics, films, foams, nonwoven webs, woven webs, paper, laminates, fiber reinforced plastics and the like, or combinations thereof. It may be preferable that the materials making up the fastening device be flexible. The flexibility is designed to allow the fastening system to conform to the shape of the body and thus, reduces the likelihood that the fastening system will irritate or injure the wearer's skin.

Figure 2:
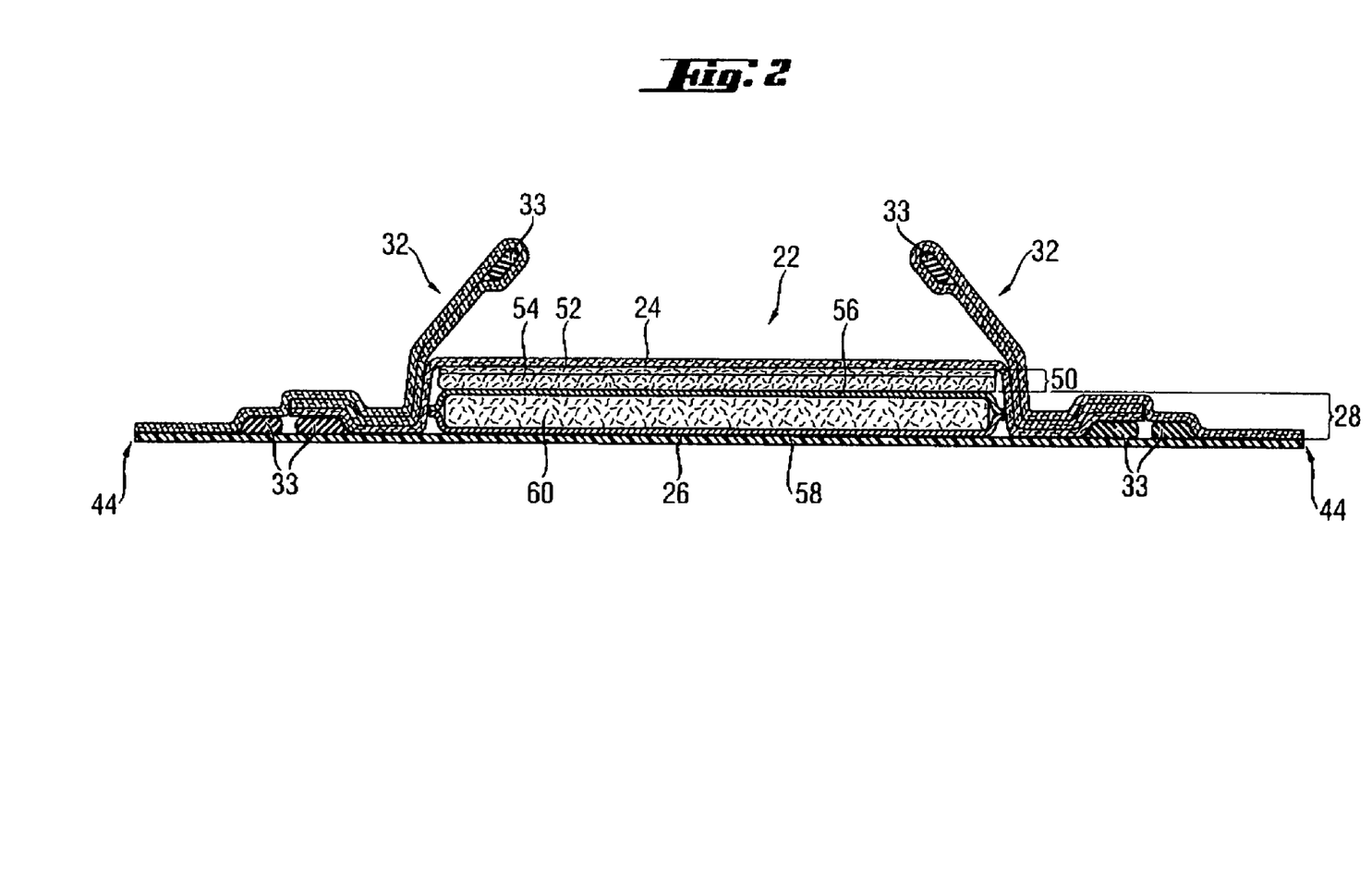
FIG. 2 is a cross-sectional view of the disposable diaper shown in FIG. 1.

FIG. 2 shows a cross-sectional view of FIG. 1 taken in the transverse axis 110. Starting from the wearer facing side the diaper comprises the topsheet 24, the components of the absorbent core 28, and the backsheet 26. The absorbent core preferably comprises an acquisition system 50, which comprises an upper acquisition layer 52 facing towards the wearer and a lower acquisition layer 54. In one preferred embodiment the upper acquisition layer comprises a non-woven fabric whereas the lower acquisition layer preferably comprises a mixture of chemically stiffened, twisted and curled fibers, high surface area fibers and thermoplastic binding fibers. In another preferred embodiment both acquisition layers are provided from a non-woven material, which is preferably hydrophilic. The acquisition layer preferably is in direct contact with the storage layer 60.

Acquisition members according to the present invention are preferably comprised by the acquisition system 50 of a diaper as described. Most preferably, the acquisition members are comprised by the upper acquisition layer 52. In one preferred embodiment of the present invention the upper acquisition layer 52 consists of the claimed acquisition member.

The storage layer 60 is preferably wrapped by a core wrap material. In one preferred embodiment the core wrap material comprises a top layer 56 and a bottom layer 58. The top layer 56 and the bottom layer 58 can be provided from a non-woven material. One preferred material is a so-called SMS material, comprising a spunbonded, a melt-blown and a further spunbonded layers. The top layer 56 and the bottom layer 58 may be provided from two or more separate sheets of materials or they may be alternatively provided from a unitary sheet of material. Such a unitary sheet of material may be wrapped around the storage layer 60, e.g. in a C-fold. The top layer 56 and the bottom layer 58 may also be joined to each other, preferably along their periphery. In one preferred option both layers are joined along their longitudinal peripheries, in other embodiments they are joined along the transversal peripheries, or along the longitudinal and the transversal peripheries. The joining can be achieved by multiple means well known in the art, eg. by adhesive means, using a continuous or a discontinuous pattern, and preferably a linear or curvilinear pattern.

The storage layer 60 typically comprises fibrous materials, mixed with super-absorbent, absorbent gelling materials. Other materials described above as suitable for the absorbent core 28 may also be comprised.

Nonwoven Fabrics

A nonwoven fabric is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled.

The fibres may be of natural or man-made origin. They may be staple or continuous filaments or be formed in situ.

Nonwoven fabrics can be formed by many processes such as meltblowing, spunbonding, carded. The basis weight of nonwoven fabrics is usually expressed in grams per square meter (gsm).

Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Fibers are classified according to their origin, chemical structure, or both. They can be braided into ropes and cordage, made into felts (also called nonwovens or nonwoven fabrics), woven or knitted into textile fabrics, or, in the case of high-strength fibers, used as reinforcements in composites—that is, products made of two or more different materials.

The nonwoven fabrics may comprise fibers made by nature (natural fibers), made by man (synthetic or man-made), or combinations thereof. Example natural fibers include but are not limited to: animal fibers such as wool, silk, fur, and hair; vegetable fibers such as cellulose, cotton, flax, linen, and hemp; and certain naturally occurring mineral fibers. Synthetic fibers can be derived from natural fibers or not. Example synthetic fibers, which are derived from natural fibers include but are not limited to rayon and lyocell, both of which are derived from cellulose, a natural polysaccharide fiber. Synthetic fibers, which are not derived from natural fibers can be derived from other natural sources or from mineral sources. Example synthetic fibers not derived from natural sources include but are not limited to polysaccharides such as starch. Example fibers from mineral sources include but are not limited to polyolefin fibers such as polypropylene, polyethylene fibers and polyester, which are derived from petroleum, and silicate fibers such as glass and asbestos.

Nonwoven webs can be formed by direct extrusion processes during which the fibers and webs are formed at about the same point in time, or by preformed fibers, which can be laid into webs at a distinctly subsequent point in time. Example direct extrusion processes include but are not limited to: spunbonding, meltblowing, solvent spinning, electrospinning, and combinations thereof typically forming layers.

Example "laying" processes include wetlaying and drylaying. Example drylaying processes include but are not limited to airlaying, carding, and combinations thereof typically forming layers. Combinations of the above processes yield nonwovens commonly called hybrids or composites. Example combinations include but are not limited to spunbond-meltblown-spunbond (SMS), spunbond-carded (SC), spunbond-airlaid (SA), meltblown-airlaid (MA), and combinations thereof, typically in layers. Combinations which include direct extrusion can be combined at about the same point in time as the direct extrusion process (e.g., spinform and coform for SA and MA), or at a subsequent point in time. In the above examples, one or more individual layers can be created by each process. For instance, SMS can mean a three layer, 'sms' web, a five layer 'ssmms' web, or any reasonable variation thereof wherein the lower case letters designate individual layers and the upper case letters designate the compilation of similar, adjacent layers.

The fibers in a nonwoven web are typically joined to one or more adjacent fibers at some of the overlapping junctions. This includes joining fibers within each layer and joining fibers between layers when there is more than one layer. Fibers can be joined by mechanical entanglement, by chemical bond or by combinations thereof. Fibers can also be joined by heat-bonding, which comprises techniques such as through-air bonding and thermobonding by use of heated calendar rolls.

All of the above described fibers and manufacturing techniques can be useful for providing an acquisition member according to the present invention.

Preferred Acquisition Members

Any material comprising a multitude of fibers and a binder, namely any non-woven material as described above is suitable for providing a liquid acquisition layer according to the present invention. The respective material must provide good recovery regarding the application and removal or external pressure. In particular, the material has improved recovery at elevated temperatures compared to materials of the prior art.

A preferred material will have a good recovery at 20° C., a temperature which is considered representative of room temperature, and thereby representative of many transport and storage conditions. A preferred material will further have good recovery values over a broad range of temperatures, namely temperatures above 20° C. A temperature of 45° C. is thought to be representative of relatively high temperature storage conditions, but the temperature is also thought to be representative for the upper end of temperatures encountered under wearing conditions. A temperature of 60° C. is thought to be representative of more extreme storage and transport conditions, as encountered in particularly high climates. Acquisition layers in accordance with the present invention will not loose an substantial amount of their ability to recover from external pressure when the material is held as a temperature of 45° C., or 60° C., respectively.

Preferred materials according to the present invention will have a recovery at 20° C. of at least 70%, more preferably of at least 75% or 80%. For preferred materials the recovery value is at 45° C. will be at least 45%, more preferably 50%, 55% or at least 60%.

According to the present invention the recovery value at 45° C. is at least 65% of the recovery value at 20° C. More preferred are higher recovery values, namely of 70%, more preferably 75%, yet more preferably 80% of the recovery value at 20° C. Preferred material will also still at 60° C. have recovery values which are high as compared to their recovery values at 20° C., preferably the recovery value at 60° C. is at least 50%, more preferably 55%, yet more preferably 60% or 65% of the recovery value at 20° C.

The recovery values of materials useful for absorbent articles, and in the present context of a liquid acquisition layer of such absorbent articles are relevant at different pressures. For example, a sitting baby will exert a pressure of about 2.1 kPa (about 0.3 psi), however, the pressure very much depending on the baby wearing the diaper and on the circumstances of its sitting. When absorbent articles, for example diapers, are shipped in plastic packaging, they are often subjected to pressures in the range of 6 to 10 kPa (about 0.9 to 1.5 psi). When materials useful for liquid acquisition layers are shipped in roll stock form, they maybe subjected to pressures up to 50 kPa (about 7 psi). Without wishing to be bound by theory it is believed that the recovery behavior of a material under very high pressures is representative also for the recovery value at lower pressures. Therefore, it is believed that a material which provides excellent recovery performance under high pressures as experienced for example by roll stock transport, will also guarantee excellent recovery behavior when taken out of a package and when being worn. Therefore, the measurements of the recovery values as described below are carried out under a pressure of 50 kPa.

Liquid acquisition layers in accordance with the present invention comprise a multitude of fibers, preferably in the form of a non-woven material and a binder. While a large variety of fibers and binders are suitable, it has been found that certain materials provide a better recovery than other materials and are therefore preferred for materials according to the present invention.

Preferred fibers according to the present invention are polyester fibers, such as PET fibers. The acquisition materials have been found to work best if a blend of different fibers is used. While a blend of 3, 4, 5 or more different fibers can be used, preferably a blend of two fibers is used. Such blend may comprise at least 10, 20, 30, 40, 50, 60, 70, 80, or 90 weight % of a first type and the remaining weight % portion of a second type of fiber. Highly preferred according to the present invention is a 50:50 blend of fibers, i.e. 50 weight percent of a first type of fibers is blended with 50 weight percent of a second type of fibers.

Preferably, at least the second type of fibers will exhibit a spiral-crimp. As used herein, a spiral-crimp is any three-dimensional crimp and preferably one wherein the fibers substantially assume a helical shape.

Optionally, the first type of fibers may also be spiral-crimped. In one embodiment of the present invention the first type of fibers and the second type of fibers are identical.

The first type of fibers may be thinner than the second type of fibers. Preferably the first type of fibers will have 3-9, more preferably 5-8, and most preferably 6-7 dtex. The second type of fibers will preferable have 8-12, more preferably 9-10 dtex. The first type of fibers and the second type of fibers may be of different length, but preferably are of the same length. Preferably, the fibers have an average length from 20-70 mm, more preferably from 30-50 mm. The first type of fibers will preferably have a higher crimp value as the second type of fibers. Preferred crimp values for the first type of fibers are 8-12 crimps per inch (cpi), and more preferably 9-10 cpi. For the second type of fibers 4-8 cpi are preferred, and 5-7 cpi are even more preferable.

A preferred first type of fibers can be obtained from Wellman, Inc. Ireland under the trade name H1311. A preferred second type of fibers can be obtained from Wellman, Inc. under the trade name T5974.

One preferred type of fibers useful in the present invention are so-called bi-component fibers, where individual fibers are provided from different materials, usually a first and a second polymeric material. The two materials may be chemically different (hence the fibers are chemically heterogeneous) or they may differ only in their physical properties while being chemically identical (hence the fibers are chemically homogeneous). For example, may the intrinsic viscosity of the two materials be different, which has been found to influence the crimping behavior of the bi-component fibers. Hence, chemically heterogeneous bi-component fibers and chemically homogeneous bi-component fibers are preferred in accordance with the present invention.

Bi-component fibers, which are especially suitable for the second type of fibers are side-by-side bi-component fibers as disclosed for example in WO 99/00098. A specifically preferred type of bi-component fiber is a fiber of circular cross section with a hollow space in the centre. It is preferred that 10-15% of the cross sectional area are hollow, more preferably 20-30% of the cross sectional area are hollow.

Preferably, at least one type of fibers and preferably two or more types of fibers are crimped. For the first type of fibers a 2D crimp or "flat crimp" is preferred. For the second type of fibers a 3D or spiral-crimp is preferred. It is believed that the use of side-by-side bi-component fibers is beneficial for imparting a spiral-crimp to the fibers.

Without wishing to be bound by theory, it is further believed that the spiral crimping of fibers is very beneficial for their liquid acquisition and distribution behaviour. It is assumed that the spiral crimp increases the void space in an acquisition member formed by such fibers. Often, an absorbent article, when being worn, is exposed to a certain pressure exerted by the wearer, which potentially decreases the void space in the acquisition member. Having good permeability and sufficient void space available are important for good liquid distribution and transport. It is further believed that the bi-component spiral-crimped fibers as described above are very suitable to maintain sufficient void volume even when an acquisition member is exposed to pressure. Also are spiral-crimped fibers believed to provide for good permeability as for a given fiber dtex value, the hollow fiber cross-section allows for a larger outer diameter of the fiber as compared to a compact cross-section. The outer diameter of a fiber appears to determine the permeability behavior of an acquisition member formed by such fibers.

While any of the above-described manufacturing processes for non-wovens are suitable to provide an acquisition member in accordance with the present invention, a highly preferred manufacturing process for such an acquisition member in both carding resin-bond technology as described in WO 98/22279. As part of this process the binder will be cured and dried after having been applied to the web.

Nonwoven materials having a basis weight from 20 to 100, preferably from 30 to 80, and most preferably from 50 to 70 gram per square meter are preferred. Basis weight is determined using a 100 cm long sample of a width given by the roll width (but at least 10 cm).

The materials of the present invention are preferably stabilized by a latex binder, and most preferably a styrene-butadiene latex binder (SB latex). Processes for obtaining such lattices are known, for example, from EP 149 880 (Kwok) and US 2003/0105190 (Diehl et al.). Preferred SB lattices, however, are obtained in using more than 10 weight % of a mono-, or bi-carboxylic acid, and will herein be referred to as having a carboxylation level of more than 10%. Preferred SB latices will have a carboxylation level from 10% to 25%, more preferably from 10% to 20%. Depending on the ultimate application of the binder level in excess of 12%, 14% or 16% are preferred. A particularly preferred SB latex is available under the trade name GENFLO™ 3160 (OMNOVA Solutions Inc.; Akron, Ohio).

Without being bound by theory, it is believed that such binders are more effective because the temperature sensitivity of the recovery value for such binders is reduced compared to other binders of the prior art. As is well known, latex binders are applied to a nonwoven structure in a liquid form that accumulates in fiber intersections. After curing, the binder forms a coherent polymeric film that stabilizes the nonwoven structure. When the nonwoven is stressed (e. g. by compression), the polymeric film resists that stress so the fibers comprising the nonwoven are inhibited from moving. If the stress causes the polymeric film to extend past its yield value the fibers can move irreversibly with resulting reduced recovery. The Applicants believe that the recovery value of the liquid acquisition layers of the present invention is less temperature sensitive because the employed binders have improved rheology, namely an improved elastic behaviour, at elevated temperatures. Therefore, the liquid acquisition layers of the present invention can recover from applied stresses instead of yielding with irrevocable fiber movement.

According to the present invention it is preferred that a film formed by the binder material has a tan δ value at 40° C. which is not greater than the tan δ value at 20° C.

Tan δ value are obtained in accordance with the test method described herein. Preferred liquid acquisition layers according to the present invention have a tan δ value at 40° which is less than 0.6, preferably less than 0.5, more preferably less than 0.4, and most preferably less than 0.3.

Without wishing to be bound by theory, it appears that tan δ values increasing with temperature lead to a loss in bulk of the liquid acquisition layer when the member is under an external pressure at an elevated temperature. It appears, that liquid acquisition members will often not recover and regain their original bulk when they have been subjected to pressure at an elevated temperature and their tan δ value at such a temperature is higher than the tan δ value at lower temperatures.

Again, without wishing to be bound by theory it also seems beneficial that films formed from binders useful for liquid acquisition members have a certain G'-curve. In one important aspect, the G' versus temperature curve should have an extended rubbery plateau. An extended rubbery plateau corresponds to a relatively constant G' value over a broad temperature range. Preferably G' is constant over a temperature range of at least 0° C. to 80° C., preferably at least 0° C. to 60° C., and most preferably at least 20° C. to 40° C. Herein, G' is considered constant, if its maximum value and its minimum value over a given range do not differ by more than 15%, preferably not more than 10%, most preferably not more than 5%.

The Applicants believe that in particular the increase of the carboxylation level as compared to prior art binders for nonwoven materials provides a G'-curve with an extended rubbery plateau. Binders with an extended rubbery plateau remain elastic up to higher temperatures. Therefore, nonwoven materials incorporating such binders can yield in response to external pressure without major re-arrangements in their fibrous structure. The Applicant believes that this contributes to their better ability to recover.

Another important aspect it is believed that binder materials must useful for the present invention will have a low glass transition temperature $T_g$. The glass transition temperature, as used herein, is measured by differential scanning calorimetry (DSC). Preferably, $T_g$ is in the range −10° C. to +10° C., more preferably −5° C. to +5° C., and most preferably from −3° C. to +1° C. A glass transition temperature $T_g$ which is well below the expected usage and storage temperatures of the liquid acquisition layers helps to maintain the rubbery like behaviour of the binder, and thereby improves the ability of the layers to recover. Because the present invention preferably employs binders having an extended rubbery plateau, the binders may have a low glass transition temperature $T_g$ and at the same time allow to act the binder in the rubbery plateau regime at elevated temperatures, such as 40° C., 60° C. or 80° C.

Test Methods

Recovery Value Measurement

Equipment: Dynamic Mechanical Analyzer 2980 in combination with a Gas Cooling Accessory (GCA) both provided by TA Instruments, USA or equivalent. The GCA uses liquid Nitrogen, which is evaporated and led through the furnace of the DMA in order to control the temperature in combination with the heater of the furnace and to provide inert measurement atmosphere. The Isothermal stability should not be less than +/−1° C.

To work in compression mode a standard compression clamp provided by TA Instruments with compression plate diameter of 15 mm is employed. The maximum compression force of the instrument should be 18N or more. The optical encoder (position sensor to determine the position of the drive shaft, which is connected to the moveable upper compression plate) delivers a strain resolution of 1 nm.

Procedure:

Sample Preparation:

Using the punch provided by TA Instruments a cylindrical sample of 13 mm diameter is punched out of the non-woven sample (NW) and placed onto the lower plate of the compression clamp. To determine the initial thickness of the NW, the upper plate is placed carefully above the NW by hand. The upper plate should not touch the NW in order to prevent uncontrolled pre-compression. After the upper plate is positioned appropriately, the motor drive shaft is blocked to keep the upper plate in position.

DMA—Compression Creep Test Method:

The Compression Creep Test consists of a compression step, where a certain stress is applied to the NW, and a subsequent recovery step, where the stress is set to zero in order to determine the resiliency or recovery of the NW.

The following method parameters are defined:

Temperature: The temperature is kept constant for the entire experiment. Experiments are typically conducted at either 20° C., 45° C. or 60° C. in order to determine temperature dependence of the recovery functions. (One experiment per temperature option.)

Equilibration time: An equilibration time of at least 10 min has to be programmed ahead the compression step in order to allow the NW and the instrument to get in thermal equilibrium Poisson ratio: 0.44

Preload force: 0.02N, applied during the entire experiment to keep upper compression clamp plate in contact with NW-sample after method start Sample measurements: Cylindrical:
  Diameter: 13 mm, determined by punch
  Thickness: To ensure defined pre-compression prior to the determination of the sample thickness for all experiments a force of 0.02N is applied for 5 seconds to the upper plate driving the upper plate against the NW. (Start method and cancel after 5 seconds blocking the drive shaft after cancellation. The compression should come to equilibrium within 20 micrometer of travel of the upper plate.). An equilibrium thickness is achieved. The distance between the lower and upper clamp plates determines the sample thickness (digital calliper, 2 digits).

Compression step time: 120 min

Stress applied: 50 kPa (about 7 psi) The DMA uses clamp correction factors in order to count for transverse strains due to dilatation effects in compression mode. The stress, which needs to be entered to receive an actual stress on the material of 50 kPa (about 7 psi) depends on sample thickness considering the clamp factors. This stress is calculated multiplying 50 kPa (about 7 psi) with the respective clamp factor at given sample thickness (table including sample thickness versus clamp factors provided by TA Instruments). The clamp factors have to be interpolated in order to match sample thickness.

Recovery step time: 120 min

Stress applied: 0 Pa

Report:
  Recovery value in % relative to the initial sample thickness ((recovered sample thickness/initial sample thickness)×100) is plotted against recovery time. The final recovery value after 120 min is reported as function of measurement temperature.

Tan $\delta$ Measurements

The tan $\delta$ value of a binder comprising a dispersion of a polymer substance in an essentially aqueous medium is measured on a polymer film prepared from said binder. For this, ca. 2% of Paragum 147 thickener are added and the dispersion is thoroughly mixed and allowed to rest for ca. 15 min. Then the film is drawn with the help of a Gardner knife and the essentially aqueous medium is evaporated in a through-air oven at 50° C. and allowed to further dry until becoming clear over night. Subsequent curing is conducted at 150° C. for 60 seconds.

The thickness of the respective film is not critical. Measurements can very well be performed on films having a thickness of 0.3 mm.

The tan $\delta$ is a rheology value well-known in the art, which can be readily measured with a variety of equipments. While tan $\delta$ corresponds to the viscous modulus $G''$ divided by the elastic modulus $G'$, the tan $\delta$ value can also be obtained without first obtaining $G'$ and $G''$ by using standard rheology equipment. A Mechanical Analyzer 2980 in combination with a Gas Cooling Accessory, both provided by TA Instruments, USA machine has been found to work well for such measurements.

Tan $\delta$ values, as used herein art those values measured in tensile mode.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven liquid acquisition layer for an absorbent article, said liquid acquisition layer comprising:
   a. 60 to 80 weight percent of polyester fibers, said fibers comprising
      i. 20 to 80 weight percent of a first type of fibers, the first type of fibers comprising flat-crimp fibers having a length of between 30 and 50 mm and 8-12 crimps per inch, and
      ii. 20 to 80 weight percent of a second type of fibers, the second type of fibers comprising spiral-crimp fibers having a length of between 30 and 50 mm and 4-8 crimps per inch; and
   b. a styrene-butadiene latex binder having a constant $G'$ over a temperature range of from 20° C. to 40° C. and a $T_g$ of between −10° C. and 10° C., wherein said liquid acquisition layer has a recovery value at 20° C. and a recovery value at 45° C., said recovery value at 45° C. being at least 65% of said recovery value at 20° C. when measured according to the Recovery Value Measurement Test.

2. The liquid acquisition layer according to claim 1 wherein the recovery value at 45° C. is at least 70% of said recovery value at 20° C.

3. The liquid acquisition layer according to claim 1, wherein the liquid acquisition layer comprises about 20 to 40 weight percent of said binder.

4. The liquid acquisition layer according to claim 1, wherein the liquid acquisition layer comprises about 20 to 40 weight percent of said binder, the second type of fibers comprising spiral-crimp fibers in the form of hollow chemically homogeneous bi-component fibers.

5. The liquid acquisition layer according to claim 1, wherein the polyester fibers are carded to form a nonwoven.

6. An absorbent article comprising:
   the liquid acquisition member of claim 1.

* * * * *

UNITED STATES PATENT AND TRADEMARK OFFICE
CERTIFICATE OF CORRECTION

| | | |
|---|---|---|
| PATENT NO. | : 7,767,598 B2 | Page 1 of 1 |
| APPLICATION NO. | : 10/913003 | |
| DATED | : August 3, 2010 | |
| INVENTOR(S) | : Schneider et al. | |

It is certified that error appears in the above-identified patent and that said Letters Patent is hereby corrected as shown below:

Column 10
Line 44, delete "wom" and insert --worn--.

Signed and Sealed this
Twenty-eighth Day of June, 2011

David J. Kappos
*Director of the United States Patent and Trademark Office*